(12) United States Patent
Kozai et al.

(10) Patent No.: US 8,852,206 B2
(45) Date of Patent: Oct. 7, 2014

(54) PROBE INSERTION DEVICE FOR IMPLANTING A PROBE INTO TISSUE

(75) Inventors: Takashi Daniel Yoshida Kozai, Ann Arbor, MI (US); Daryl R. Kipke, Pinckney, MI (US); Jeyakumar Subbaroyan, Parsippany, NJ (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1518 days.

(21) Appl. No.: 12/483,313

(22) Filed: Jun. 12, 2009

(65) Prior Publication Data

US 2009/0312770 A1 Dec. 17, 2009

Related U.S. Application Data

(60) Provisional application No. 61/060,928, filed on Jun. 12, 2008.

(51) Int. Cl.
| | | |
|---|---|---|
| *A61B 5/04* | (2006.01) | |
| *A61B 5/00* | (2006.01) | |
| *A61B 17/34* | (2006.01) | |
| *A61B 17/00* | (2006.01) | |
| *A61B 17/16* | (2006.01) | |
| *A61N 1/05* | (2006.01) | |
| *A61B 19/00* | (2006.01) | |

(52) U.S. Cl.
CPC ..... *A61B 17/3468* (2013.01); *A61B 2017/0084* (2013.01); *A61B 5/6846* (2013.01); *A61B 17/1604* (2013.01); *A61N 1/0529* (2013.01); *A61B 19/20* (2013.01)
USPC ......................................... 606/129

(58) Field of Classification Search
CPC ........... A61B 17/1604; A61B 17/3468; A61B 5/6846; A61B 5/686; A61B 5/6847; A61B 2017/0084; A61B 2017/00938; A61N 1/0529
USPC ............. 606/108, 129; 604/57; 600/372–397; 607/115–138; 623/1.11, 1.12, 1.23
See application file for complete search history.

(56) References Cited

U.S. PATENT DOCUMENTS

| | | | |
|---|---|---|---|
| 3,405,715 A | | 10/1968 | Hagfors |
| 6,324,414 B1 * | | 11/2001 | Gibbons et al. ............... 600/373 |
| 6,689,141 B2 * | | 2/2004 | Ferrera et al. ................. 606/108 |
| 2002/0072737 A1 * | | 6/2002 | Belden et al. ................. 606/129 |
| 2003/0100823 A1 * | | 5/2003 | Kipke et al. .................. 600/378 |

OTHER PUBLICATIONS

Foley CP, Neeves KB, Saltzman WM, Olbricht WL. Bioerodible scaffolds for implantable microfluidic probes in convection enhanced neural drug delivery. In: AIChE Annual Meeting; 2006.

(Continued)

*Primary Examiner* — Kathleen Holwerda
*Assistant Examiner* — Sarah W Aleman
(74) *Attorney, Agent, or Firm* — Harness, Dickey & Pierce, P.L.C.

(57) ABSTRACT

A probe insertion device for implanting a probe into tissue includes a rigid base that selectively attaches to the probe due to a bond between the base and the probe, that provides a structural backbone to the probe, is longitudinally aligned with the probe, and can be adapted to receive a fluid between the base and the probe. The probe insertion device can include a surface covering at least a portion of the base that reduces the bond between the base and the probe in the presence of the fluid.

21 Claims, 7 Drawing Sheets

(56) References Cited

OTHER PUBLICATIONS

Lee KK, He JP, Singh A. Massia S. Ehteshami G, Kim B, et al. Polyimide-based intracortical neural implant with improved structural stiffness. J. Micromech Microeng 2004; 14:32-7.

O'Brien DP, Nichols TR, Allen MG. Flexible microelectrode arrays with integrated insertion devices. 14th IEEE international conference on micro electro mechanical systems. Technical Digest 2001:216-9.

Suzuki T, Mabuchi K, Takeuchi S. A 3D flexible parylene probe array for multichannel neural recording. In: Neural Engineering, Proceedings of the 1st international IEEE EMBS; 2003, p. 154-6.

Takeuchi S, Yoshida Y. Ziegler D, Mabuchi K, Suzuki T. Parylene flexible neural probe with micro fluidic channel. Mems 2004: 17th IEEE international conference on micro electro mechanical systems. Technical Digest 2004: 208-11.

\* cited by examiner

PROBE INSERTION DEVICE FOR IMPLANTING A PROBE INTO TISSUE

CROSS-REFERENCE TO RELATED APPLICATIONS

This application claims the benefit of U.S. Provisional Application No. 61/060,928, filed 12 Jun. 2008, which is incorporated in its entirety by this reference.

GOVERNMENT RIGHTS

This invention was made with government support under EB002030 awarded by the National Institutes of Health. The government has certain rights in the invention.

TECHNICAL FIELD

This invention relates generally to the implantable device field, and more specifically to an improved system and method of implanting probes into tissue in the implantable probe field.

BACKGROUND

This section provides background information related to the present disclosure which is not necessarily prior art.

There is an ongoing need for higher fidelity and longer lasting implantable microscale neural interfaces for recording and stimulation both in academic and emerging clinical applications, such as deep brain stimulation. For long term chronic applications of probes, one challenge is to improve and/or control the degree to which an implanted probe integrates with the surrounding tissue to meet particular performance requirements, such as high signal-to-noise ratio and long-term stability. Computer models and experimental studies of the probe-tissue interface suggest that nonrigid, flexible and soft probes, such as those made of biocompatible polymers that approach the brain's bulk material characteristics, may help to minimize the relative micromotion between the probe and surrounding tissue that may damage tissue and improve performance and/or tissue health. In addition to using flexible and soft probes, utilizing advanced probe architectures with sub-cellular sized features has been shown to elicit smaller reactive tissue responses, facilitating improved long term probe-tissue integration and long term functionality of the device.

However, there are challenges in reliably implanting a probe that is soft, flexible and/or sub-cellular sized without damaging brain tissue. For example, polymer probes that are suitably flexible for long term implantation tend to buckle and/or deflect while being directed to implantation in their target areas. Existing implantation strategies of soft and flexible probes include integrating a rigid structure within the probe, coating the probe with stiff biodegradable polymers or crystals, and filling channels within the probe with stiff biodegradable elements. However, it is difficult for these strategies to achieve the critical probe stiffness required for successful insertion into tissue, and may incur more tissue damage due to a larger implanted footprint. Furthermore, these existing implantation methods of soft and flexible probes restrict probe design, restrict probe functionality, or negate the desired probe flexibility.

Thus, there is a need in the implantable probe field to create an improved device for implanting nonrigid probes. This invention provides such an improved probe insertion device.

BRIEF DESCRIPTION OF THE FIGURES

The drawings described herein are for illustrative purposes only of selected embodiments and not all possible implementations, and are not intended to limit the scope of the present disclosure.

Corresponding reference numerals indicate corresponding parts throughout the several views of the drawings.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Probe Insertion Device

Figure 1A:
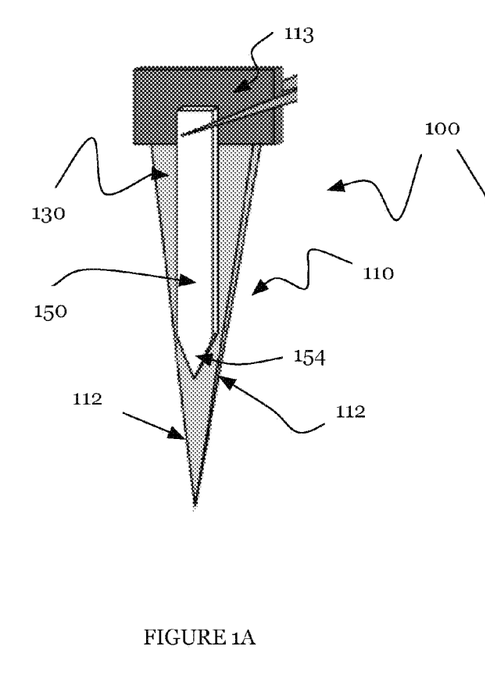
FIG. 1A is a schematic representation of the probe insertion device of the preferred embodiment.
Figure 1B:
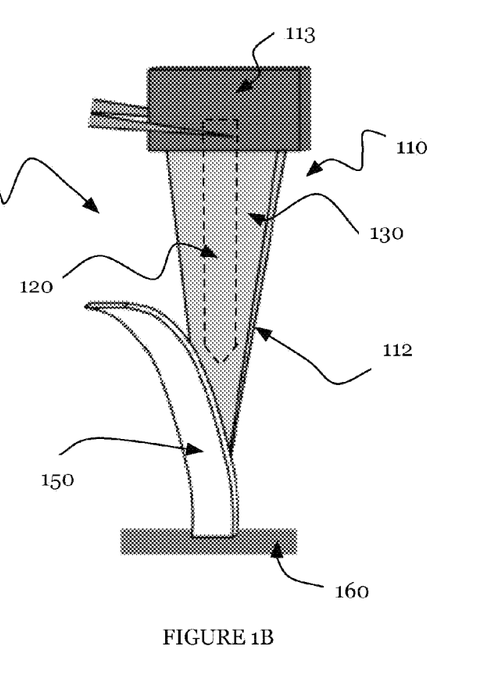
FIG. 1B is a schematic representation of the probe insertion device of the preferred embodiment, shown in the process of removing the base from the tissue.
Figure 2:
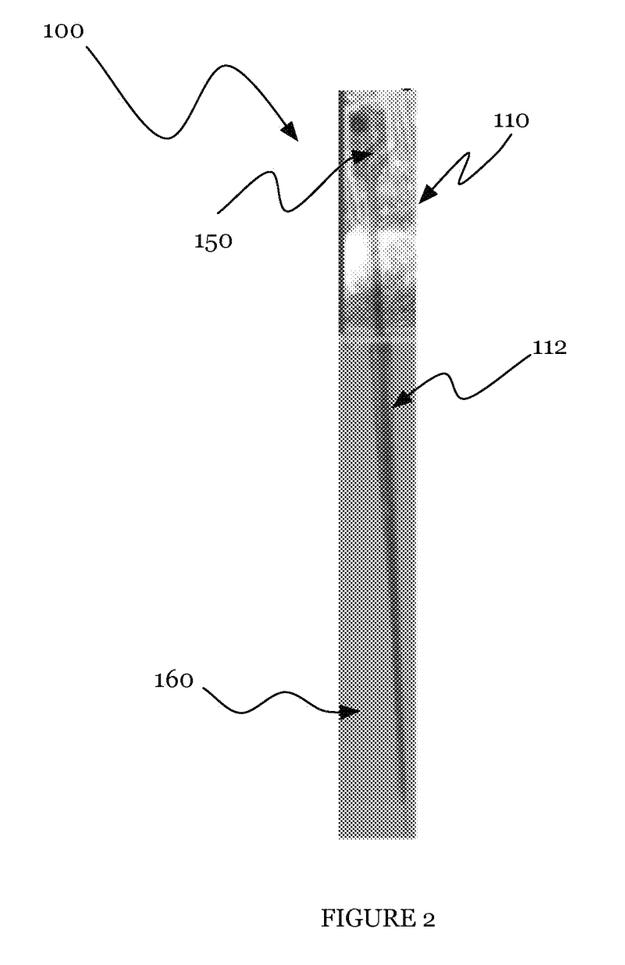
FIG. 2 is a front view of the probe insertion device of the preferred embodiment implanted in tissue.
Figure 3A:
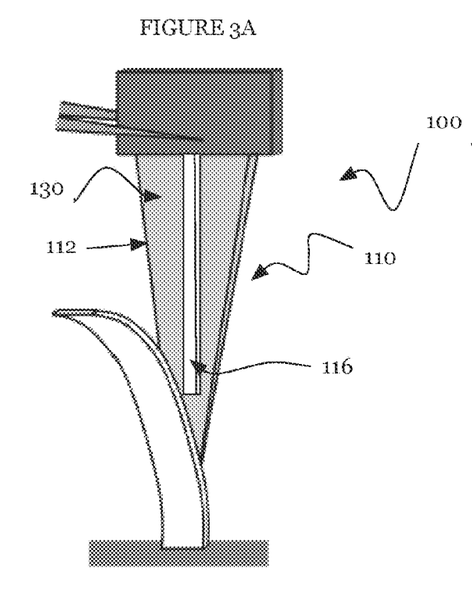
FIGS. 3A and 3B are schematic representations of the probe insertion device with a ridge and a groove, respectively.
Figure 3B:
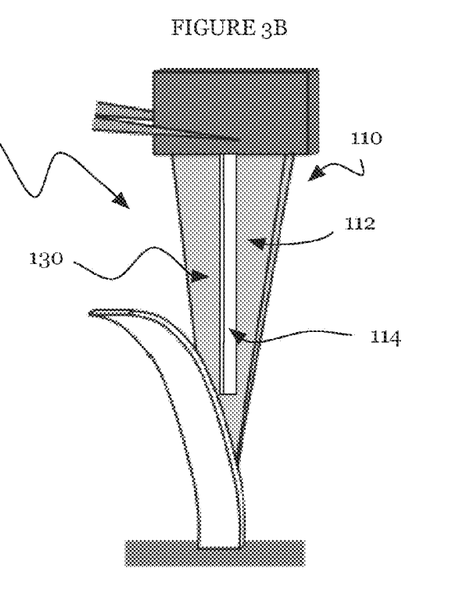

As shown in FIGS. 1A and 1B, the probe insertion device 100 of the preferred embodiments preferably includes a rigid base 110 that attaches to a probe 150 through a bond and functions to provide a structural backbone to the probe during implantation into tissue 160, and a surface 130 on the base 110 that functions to reduce the bond between the base 110 and the probe 150 in the presence of certain fluids. The probe insertion device 100 of the preferred embodiments preferably assists the implantation of soft, flexible neural probes made of biocompatible hydrophobic polymers, such as polyimide, Parylene-C, and polydimethylsiloxane (PDMS), into neural tissue. The probe insertion device may, however, alternatively assist the implantation of flexible probes with a hydrophobic surface, microprobes that have sub-cellular sized features, highly compressible probes, blunt-tipped probes, or any other suitable kind of probe into any suitable kind of biological tissue. Probe systems are known and used in the art, such as that described in U.S. Pat. No. 3,405,715 entitled "Implantable electrode", which is incorporated in its entirety by this reference. To assist implantation of the probe 150, the base 110 of the probe insertion device 100 preferably temporarily attaches to the probe 150 to provide the probe with structural support that resists buckling and/or deflection of the probe during insertion of the probe-base assembly into tissue 160. After the probe 150 is positioned at the target area in the tissue, the base 110 is detached from the probe 150 and removed from the tissue 160 independent of the probe 150, leaving the probe 150 in its implanted position. Fluid 126 is preferably introduced to chemically enhance the separation process of the base 110 from the probe 150, which eases removal of the base 110 from the tissue 160 without displacing the probe 150. Since the base 110 is removed from the tissue 160, the probe insertion device 100 may also be reusable for implanting additional probes.

The base 110 of the probe insertion device 100 can attach to a probe 150 through a bond between the base the probe and functions to provide a structural support to the probe 150 during implantation of the probe 150. The base 110 can bond to a probe 150 through several different types of suitable bonds. One of the suitable bonds can be electrostatic forces, including hydrophobic interactions. In an aqueous environment such as brain tissue, two hydrophobic materials tend to become strongly adhered to each other due to an intrinsic attractive force. This attractive force, at least in part, is the result of the formation of a convex-shaped meniscus formed between the two hydrophobic materials. In order to overcome the attractive force and separate the two hydrophobic materials, hydrogen bonds must be broken to break the surface tension of the meniscus, which requires an external energy input. In the preferred embodiments, when the base 110 is attached to the probe 150 through hydrophobic interactions and inserted in the brain, the meniscus is formed at the triple junction between the base, probe, and extracellular fluids. However, the base 110 may additionally and/or alternatively attach to the probe 150 through other kinds of suitable bonds. Other suitable bonds include chemical bonds such as covalent bonding, ionic bonding, metallic bonding, van der Waals bonding, hydrogen bonding, or any other suitable kind of chemical bonding. The base 110 may additionally and/or alternatively attach to the probe 150 through one or more other kinds of suitable bonds besides chemical bonding, including the "pin effect" in which an uneven surface tends to prevent fluid from entering small cracks at the atomic level, through a biodegradable adhesive coating, through another suitable biodegradable coating, through suction forces, micromechanical structures (including pincers and hooks), and/or through other suitable forces. The base 110 is preferably made of a material rigid enough to provide structural support to the probe 150 during insertion of the probe 150 into tissue 160, but may alternatively be made of any suitable material and additionally and/or alternatively include a scaffold, framework, or other structure to increase rigidity of the base 110. The base 110 can be made of silicon, which is both hydrophobic and rigid, but may alternatively be made of steel or another suitable material.

As shown in FIGS. 1-4, the base 110 can include a blade 112 that is flat and straight, and is adapted to be generally longitudinally aligned with the probe 150, such that the base 110 serves as a backbone for structural support of the probe 150 along the entire length of the probe. The base 110 preferably attaches to a single probe 150, but may alternatively attach to multiple probes for simultaneous implantation of multiple probes. The boundaries of the base 110 can be flush with and/or extend beyond the boundaries of the probe 150, such that the probe 150 is less likely to catch on tissue 160 during insertion. As shown in FIGS. 1-4, to accomplish this, the minimum width of the base 110 can be equal to or wider than the maximum width of the probe 150 and can be attached to the probe 150 such that the probe 150 is centered in the base 110. Furthermore, as shown in FIG. 1A, the tip of the blade 112 that penetrates the tissue 160 can be flush with or extends beyond the insertable end 154 of the probe 150. The base 110 may additionally include markings that provide guidance to position the probe 150 properly on the base 110. The base 110 can be smooth and flat at the probe interface surface 120, defined as the area on the base 110 where the base 110 attaches to the probe 150. The base may, however, alternatively and/or additionally include at least one groove 114, channel, ridge 116, and/or other textured surface feature on the probe interface surface 120 that decreases the overall area of contact between the base 110 and the probe 150, which functions to increase the ease of separation of the base 110 from the probe 150 after insertion into tissue 160. The base 110 can include a material at its proximal end or other suitable grasping area 113 that includes a durable material, a textured gripping surface, and/or other suitable adaptation to be held by microforceps or another grasping suitable tool. The base 110 can be tapered to create a sharp tip that can easily penetrate tissue. However, the base 110 may alternatively have any suitable size and shape. As one example, a base 110 shaped with multiple blades may be used to simultaneously penetrate tissue 160 for implantation of multiple probes, with one or more probes on each blade.

Figure 4:
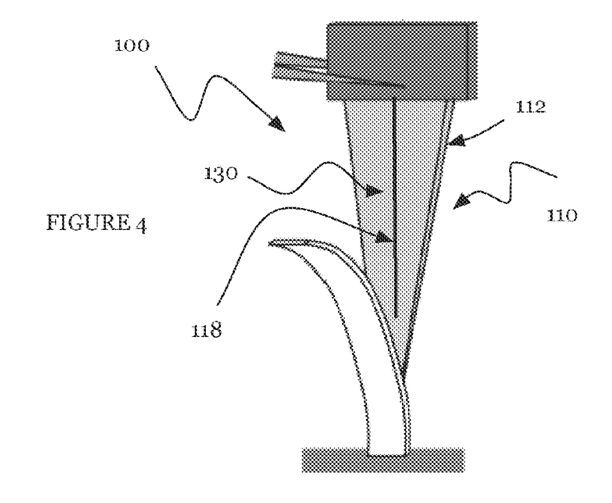
FIG. 4 is a schematic representation of the probe insertion device with a fluidic channel.
Figure 5A:
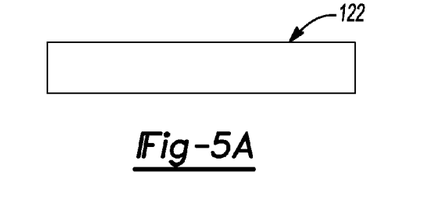
FIG. 5 is a schematic representation of the manufacturing steps of an example of the surface of the base of the probe insertion device of the preferred embodiment.
Figure 5B:
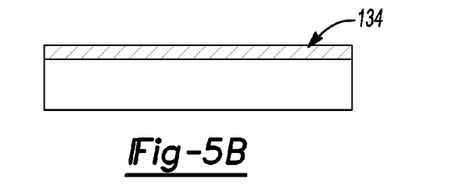
Figure 5C:
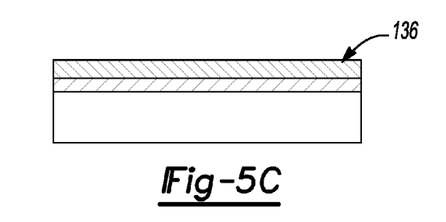
Figure 5D:
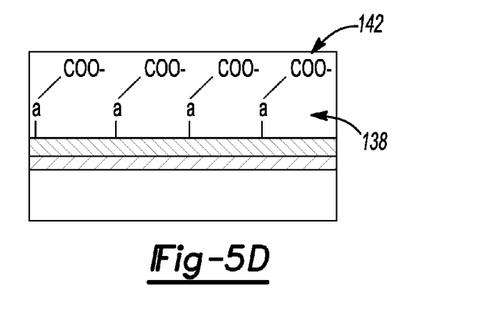
Figure 5E:
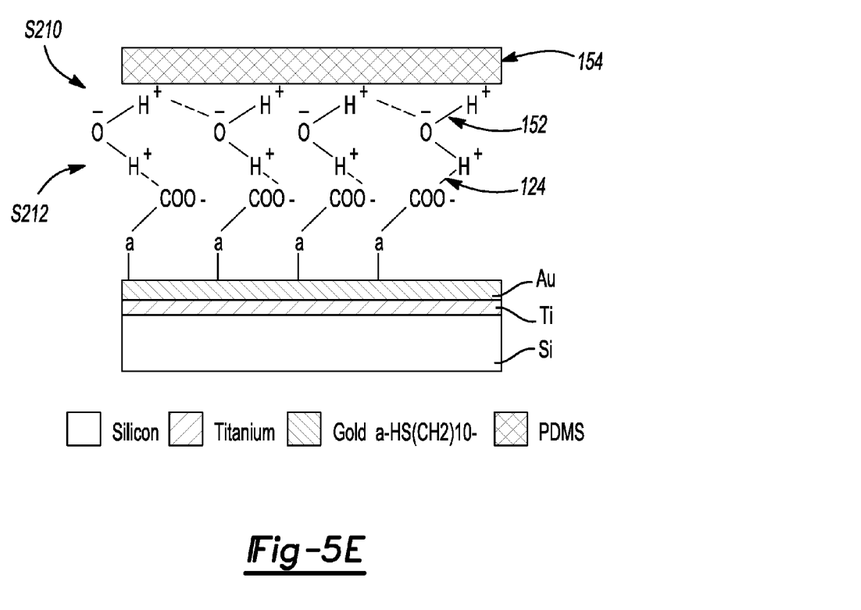

In some embodiments, the base 110 is adapted to receive a fluid 126 between the base 110 and the probe 150. The fluid can be artificial cerebrospinal fluid (ACSF), but may alternatively be any suitable fluid that is aqueous, biocompatible, isotonic, and/or has a pH similar to the natural extracellular environment of the brain. When the base 110 is attached to the probe 150 through hydrophobic interactions and receives ACSF, the water molecules in the ACSF enhances separation of the base 110 and the probe 150, as further discussed below. In some embodiments, the base 110 is adapted to receive a drop of fluid on the probe interface surface 120 between the base 110 and the probe 150, but may alternatively include a recess or other suitable receptacle to receive the fluid. As shown in FIG. 4, the base may alternatively and/or additionally include least one fluidic channel 118 that accurately directs fluid to a targeted area between the base 110 and the probe 150.

The surface 130 on the base 110 of the probe insertion device 100 can function to reduce the bond between the base and the probe in the presence of certain fluids. The surface can cover at least a portion of the base 110 that includes the probe interface surface 120. The surface preferably includes coating 132 that includes a substrate layer, a base layer, and a chemical modifier layer.

Figure 6:
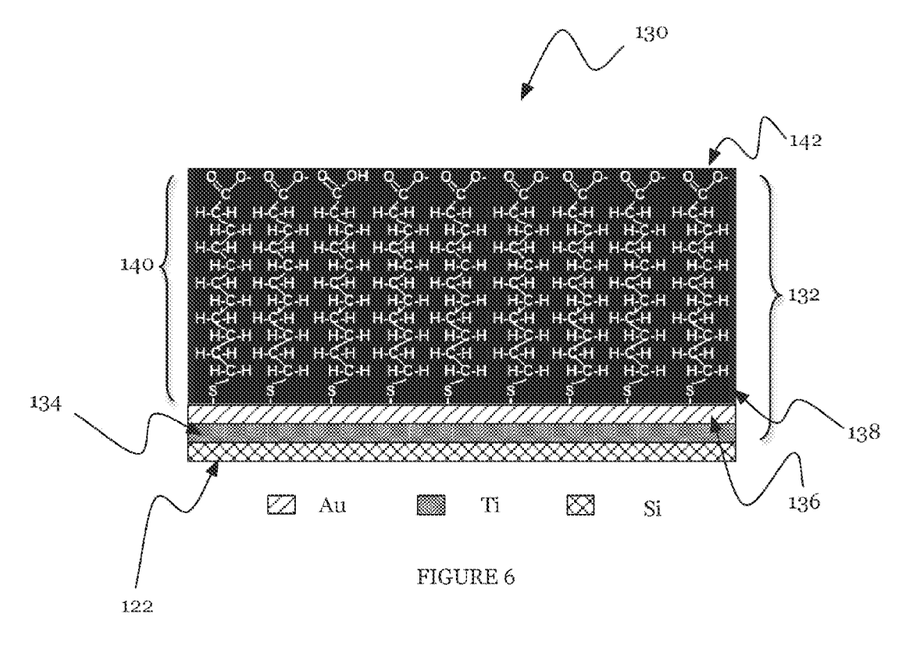
FIG. 6 is a detailed chemical schematic of the surface of the base of the probe insertion device of the preferred embodiment.

The substrate layer 134 of the coating 132 functions to enhance application of the base layer 136, by improving the chemical adhesion of the base layer 136 to the surface. As shown in FIGS. 5 and 6, the substrate layer 134 may include titanium, but may alternatively include chromium or any other suitable biocompatible material. The substrate layer 134 can be approximately 1000 angstroms thick and applied to the surface with resistive evaporation, but may alternatively be any suitable thickness and applied to the surface with any one or more thin film deposition processes, which are known by those ordinarily skilled in the art, or another suitable method.

The base layer 136 of the surface functions to facilitate the formation of the chemical modifier layer 138 on the surface, by serving as a base on which functional groups of the chemical modifier layer 138 can assemble. As shown in FIGS. 5 and 6, the base layer 136 can include gold, but may alternatively include any other suitable biocompatible material. The base layer can be approximately 100 angstroms thick and, like the substrate layer 134, can be applied to the surface 130 with resistive evaporation, but may alternatively be any suitable thickness and applied to the surface with any one or more thin film deposition processes, which are known by those ordinarily skilled in the art, or another suitable method.

The chemical modifier layer 138 of the surface 130 functions to reduce the bond between the base 110 and the probe 150. The chemical modifier layer 138 can include a highly hydrophilic, electronegative self-assembled monolayer (SAM) 140 that reduces electrostatic attraction between the base 110 and the probe 150. The hydrophilic SAM 140 can attract water molecules that exist in the tissue. Capillary action along the hydrophilic SAM-covered surface can form a concave-shaped meniscus that drives fluid between the base 110 and the probe 150 to overcome the adhesive meniscus force along the hydrophobic probe surface. The introduction of ACSF between the base 110 and the probe surface further increases the number of water molecules present and enhances separation of the base 110 and the probe 150. The SAM 140 also preferably reduces the adhesion between the base and the probe by reforming new hydrogen bonds and releasing energy in the process, which is sufficient energy input into the system to break hydrogen bonds that are among the hydrophobic interactions that attach the base 110 to the probe 150. As shown in FIG. 6, the chemical modifier layer 140 can be 11-Mercaptoundecanoic acid applied to the surface 130 as a SAM 140. 11-Mercaptoundecanoic acid is a biocompatible carboxyl acid that provides a carboxyl group 142 to reform hydrogen bonds. Since the extracellular environment of brain tissue typically has an acid disassociation constant (pKa) of 7.2 and carboxyl groups typically have a pKa of approximately 6.5, the carboxyl group terminus of the SAM 140 is typically depronated and negatively charged, which is desirable to enhance separation of the base 110 and the probe 150. However, the chemical modifier layer 140 may additionally and/or alternatively include any other carboxyl acid or suitable substance that is biocompatible, hydrophilic, and/or electronegative and applied to the surface in any suitable manner. The chemical modifier layer 140 may also include any suitable substance, applied to the surface 130 in any suitable process, that reduces chemical bonds between the base and the probe, such as one that cleaves covalent or ionic bonds present between the base and the probe.

2. Example of Manufacture

As one very specific example of the manufacture of the probe insertion device, the base is a modified "Michigan"-style thin-film silicon substrate neural probe and the coating includes a SAM of 11-mercaptoundecanoic acid. The base has a penetrating shank that is 15 micrometers thick, 1 centimeter long, and has a maximum width of 400 micrometers that gradually tapers to a penetrating tip. Prior to application of the substrate layer, base layer, and chemical modifier layer, each base is mounted onto a blank printed circuit board (PCB) and attached to a bare silicon wafer using polyimide (Kapton) tape. The bare silicon wafer undergoes the same surface treatment processes that the base undergoes, and provides a sample that can be inspected after manufacture to confirm desired surface characteristics. As shown in FIG. 6, the flat surfaces of the silicon bases and the silicon wafer are coated with a 100 angstrom thick layer of titanium, followed by a 1000 angstrom thick layer of gold through resistive evaporation. The polyimide tape is removed, and the gold-coated base and wafer are immersed together in 1 mM (millimole) ethanolic solution of 11-mercaptoundecanoic acid for 48 hours. After immersion in the acid solution, the base and wafer are rinsed in a series of rinses: a first rinse in ethanol for 5 minutes, a second rinse in ethanol for 5 minutes, a 0.1-M hydrochloric acid rinse, and a deionized water rinse.

Figure 7:
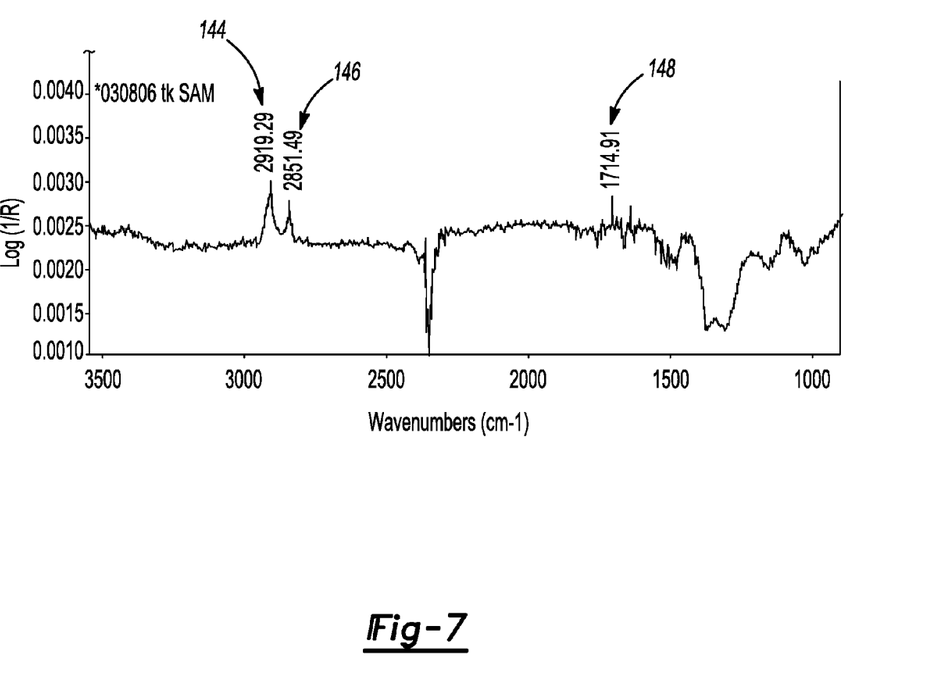
FIG. 7 is a representative IR spectrum of the surface of the base in an example of the probe insertion device of the preferred embodiment.

To confirm that the base is coated with the SAM, a wafer fragment from the manufacturing process is inspected and compared to a 1 cm×1 cm gold coated wafer using infrared spectroscopy. As shown in the representative IR spectrum of FIG. 7, there are three peaks characteristic of an 11-mercaptoundecanoic SAM-coated wafer or base: two peaks 144 and 146 at wavenumbers 2919 $cm^{-1}$ and 2851 $cm^{-1}$ are characteristic of the hydrocarbon backbone of 11-mercaptoundecanoic acid, and one peak 148 at 1714 $cm^{-1}$ is characteristic of the carboxyl group 142. If inspection of the wafer fragment from the manufacturing process produces an IR spectrum similar to the representative IR spectrum, the probe insertion device is successfully coated with the SAM as desired. Following inspection, the SAM-coated base and wafer can be stored in ethanol for up to one week before use.

3. Method of Implanting a Probe Into Tissue

Figure 8A:
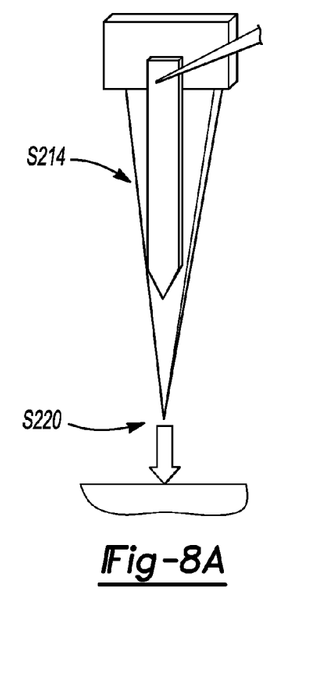
FIGS. 8A through 8D are partial schematic representations of the method of implanting a probe with the probe insertion device of the preferred embodiment.

As shown in FIGS. 5 and 8A through and 8D, the method of implanting a probe into tissue can include the steps of attaching a rigid base to the probe S210, inserting at least a portion of the probe into the tissue S220, decoupling at least a portion of the probe from the base S230, allowing a fluid to flow between the base and the probe to induce detachment of the base from the probe S240, and withdrawing the base from the tissue S250. The method preferably applies to implantation of flexible probes, including polymer probes made of hydrophobic materials such as PDMS, Parylene-C, and polyimide, but may additionally apply to implantation of flexible probes made of other materials, microprobes that have subcellular sized features, highly compressible probes, blunt-tipped probes, or any suitable kinds of probes.

The step of attaching a rigid base to the probe S210 functions to provide a structural backbone to the probe. The step of attaching a rigid base to the probe S210 can include attaching the base to the probe with electrostatic forces S212 and positioning the probe such that the base is flush with or extends beyond the edges of the probe S214. The electrostatic forces attaching the base to the probe can be due to hydrophobic interactions between the base and the probe. However, the step of attaching a rigid base to the probe S210 may additionally and/or alternatively include attaching the base to the probe through other kinds of chemical bonds such as covalent bonding, ionic bonding, metallic bonding, van der Waals bonding, hydrogen bonds, or any other suitable bonds. Further, the step of attaching a rigid base to the probe S210 may additionally and/or alternatively include attaching the base to the probe through one or more other kinds of suitable bonds besides chemical bonding, including the "pin effect" in which an uneven surface tends to prevent fluid from entering small cracks at the atomic level, through a biodegradable adhesive coating, through another suitable biodegradable coating, through suction forces, micromechanical structures (including pincers and hooks), and/or through other suitable forces. As shown in FIGS. 8A through 8D, microforceps can be used to manually place the probe onto the surface of the base, but probe placement may alternatively be performed by an automated system or other suitable process, and may alternatively occur significantly in advance of probe insertion to create pre-made base-probe assemblies ready for implantation.

The step of attaching the base to the probe such that the base is flush with or extends beyond the edges of the probe S214 functions to reduce the tendency of the probe to catch on tissue during insertion. As shown in FIG. 8A, the base can be attached to the probe such that the base and the probe are generally longitudinally aligned and the probe is approximately centered on the base. The base can be attached to the probe such that the edges of the base, including the penetrating tip of the base, are flush with or extend beyond the tip of the probe. However, the base and the probe may alternatively be positioned in any suitable relative orientation.

The step of attaching a rigid base to the probe may additionally include the steps of applying a drop of 70% ethanol onto the base and drying the base-probe assembly in air. The drop of ethanol, in some instances, may ease adjustment of probe position on the base.

As shown in FIG. 8A, the step of inserting at least a portion of the probe into the tissue S220 function to position the probe for recording, stimulation, and/or any other appropriate actions. The step can be performed in a controlled, automated process with microforceps, but may alternatively be performed with clips, clamps, or another suitable grasping tool. The step may additionally and/or alternatively be performed with the use of dissolvable biodegradable glue or other suitable adhesive that temporarily attaches the base to the grasping tool. The step may alternatively be performed manually with a suitable grasping tool. The microforceps can grasp the base at the most proximal end during insertion, but may alternatively grasp closer to the end of the base that is inserted into tissue, or any suitable location along the base-probe assembly. The depth and speed at which the probe is inserted into the tissue, as well as the target area of the tissue, depend on the specific application of the probe. The specific parameters of implantation are well known to one ordinarily skilled in the art.

Figure 8B:
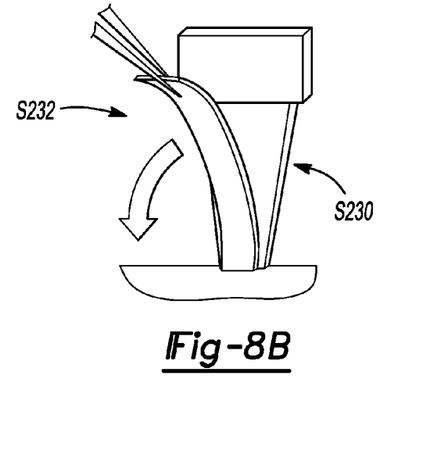

As shown in FIG. 8B, the step of decoupling at least a portion of the probe from the base S230 functions to facilitate subsequent step S240. The step includes peeling at least a portion of the probe from the base S232, preferably to the surface of the tissue, but alternatively any suitable portion of the probe. Peeling the probe from the base to the surface of the tissue can be performed manually using microforceps, but may be performed through any suitable process. In alternative versions of the method, the step of decoupling at least a portion of the probe may be modified or eliminated depending on the requirements for step S240.

Figure 8C:
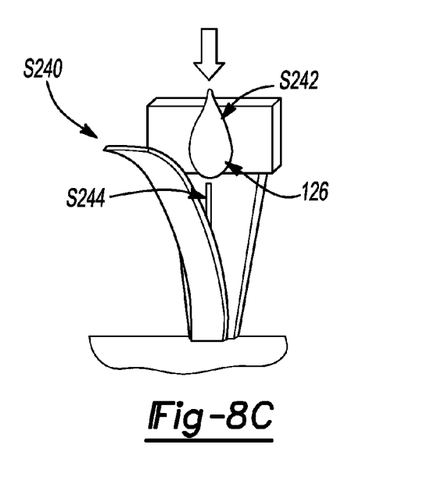
Figure 8D:
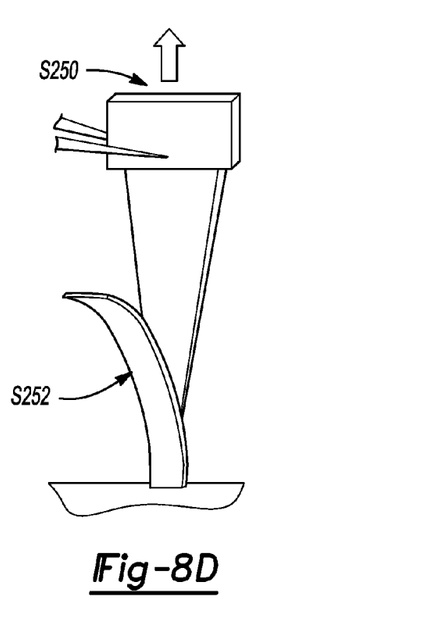

As shown in FIG. 8C, the step of allowing a fluid to flow between the base and the probe S240 functions to induce detachment of the base from the probe S240. The step preferably includes introducing a fluid that reduces the bond, such as the electrostatic attraction, between the base and the probe S242. The fluid can reduce electrostatic attraction between the base and the probe by introducing water molecules that reduce hydrophobic interactions and thereby reduce adherence of the base to the probe, but may alternatively reduce the bond between the base and the probe through any suitable process. The fluid can be introduced by placing a drop of fluid onto the base between the base and the probe near the surface of the tissue, near the "peeling" of step S230. The fluid can be artificial cerebrospinal fluid, but may alternatively be saline or any suitable fluid that is aqueous, biocompatible, isotonic, and/or has a pH similar to the natural extracellular environment of the brain. The step of allowing a fluid to flow between the base and the probe to induce detachment of the base from the probe S240 may alternatively include introducing additional drops of fluid until a meniscus can be observed between the base and the probe, and/or until the craniotomy is filled. The step of allowing a fluid to flow between the base and the probe to induce detachment of the base from the probe S240 may alternatively and/or additionally include introducing a fluid through a channel S242 in the base that delivers the fluid between the base and the probe. In this version of step S240, the method may be performed without step S230.

The step of withdrawing the base from the tissue S250 can include withdrawing the base from the tissue without displacing the probe S252. The base can be detached from the probe, and can be slowly removed from the tissue. The step of withdrawing the base from the tissue S250 can be performed in a controlled, automated process with microforceps, but may alternatively be performed with clips, clamps, or another suitable grasping tool. The step of withdrawing the base from the tissue S250 may alternatively be performed manually with a suitable grasping tool. The speed at which the base is removed from the tissue, and other parameters relevant to removal, may depend on the specific application and are known to one ordinarily skilled in the art.

As a person skilled in the art will recognize from the previous detailed description and from the figures and claims, modifications and changes can be made to the preferred embodiments of the invention without departing from the scope of this invention defined in the following claims.

We claim:

1. A probe insertion device for implanting a probe into tissue, comprising:
    a flexible neural probe including an insertable end that is implantable into tissue;
    a rigid base being a flat blade that selectively attaches to the probe along at least a length portion of the probe due to a bond between the base and the probe and provides a structural backbone to the probe; wherein the rigid base is adapted to receive a fluid between the base and the probe; and
    a surface covering at least a portion of the base that reduces the bond between the base and the probe in the presence of the fluid, thereby allowing the detachment of the base from the probe.

2. The probe insertion device of claim 1, wherein the rigid base selectively attaches to the probe due to a hydrophobic interaction between the base and the probe.

3. The probe insertion device of claim 1, wherein the rigid base selectively attaches to the probe due to a chemical bond between the base and the probe selected from the group consisting of covalent bonds, ionic bonds, metallic bonds, van der Waals bonds, and hydrogen bonds.

4. The probe insertion device of claim 1, wherein the base includes a generally straight blade.

5. The probe insertion device of claim 4, wherein edges of the base are flush with or extend beyond edges of the probe.

6. The probe insertion device of claim 1, wherein the base is made of a hydrophobic material.

7. The probe insertion device of claim 6, wherein the base is made of silicon.

8. The probe insertion device of claim 1, wherein the base includes at least one of a groove and a ridge that decreases the area of contact between the base and the probe.

9. The probe insertion device of claim 1, wherein the base includes a channel that delivers the fluid to the base.

10. The probe insertion device of claim 1, further comprising artificial cerebrospinal fluid, and wherein the rigid base is adapted to receive the artificial cerebrospinal fluid.

11. The probe insertion device of claim 1, wherein the probe includes an insertable end implantable into tissue; and wherein the base is flush with or extends beyond the insertable end of the probe.

12. The probe insertion device of claim 11, wherein the probe is made of a nonrigid material selected from the group consisting of a compressive material and a flexible material.

13. The probe insertion device of claim 12, wherein the probe includes a hydrophobic surface.

14. A probe insertion device for implanting a probe into tissue, comprising:
    a flexible neural probe including an insertable end that is implantable into tissue;
    a rigid base being a blade that selectively attaches to the probe along at least a length portion of the probe due to a bond between the base and the probe and provides a structural backbone to the probe; wherein the rigid base is adapted to receive a fluid between the base and the probe; and a surface covering at least a portion of the base that reduces the bond between the base and the probe in the presence of the fluid, thereby allowing the detachment of the base from the probe, wherein the surface includes a coating; wherein the coating includes a chemical modifier layer that reduces the bond between the base and the probe.

15. The probe insertion device of claim 14, wherein the chemical modifier layer is a hydrophilic self-assembled monolayer.

16. The probe insertion device of claim 15, wherein the hydrophilic self-assembled monolayer provides a carboxyl group.

17. The probe insertion device of claim 14, wherein the coating further includes at least one base layer that facilitates the formation of the chemical modifier layer.

18. The probe insertion device of claim 17, wherein the base layer includes gold.

19. The probe insertion device of claim 14, wherein the coating further includes at least one substrate layer that enhances the application of the base layer.

20. The probe insertion device of claim 19, wherein the substrate layer includes titanium.

21. A probe insertion assembly for implanting a probe into tissue, comprising:

a flexible neural probe including an insertable end that is implantable into tissue, wherein the probe is made of a hydrophobic polymer;

a rigid silicon microelectrode base that attaches to the probe due to electrostatic attraction and provides a structural backbone to the probe; wherein the base includes a single shank that gradually tapers; wherein the edges of the base are flush with or extend beyond the edges of the probe; wherein the probe and the base are generally longitudinally aligned and the base extends beyond the insertable end of the probe; wherein the base is adapted to receive artificial cerebrospinal fluid between the base and the probe; and a coating covering at least a portion of the base; wherein the coating includes a layer of 11-Mercaptoundecanoic acid that reduces electrostatic attraction between the base and the probe in the presence of artificial cerebrospinal fluid; wherein the coating further includes a layer of gold that facilitates formation of the 11-Mercaptoundecanoic acid layer; wherein the coating further includes a layer of titanium that enhances the application of the gold layer.

* * * * *